(12) United States Patent
Vermeire et al.

(10) Patent No.: US 7,317,317 B1
(45) Date of Patent: Jan. 8, 2008

(54) SHIELDED MICRO SENSOR AND METHOD FOR ELECTROCHEMICALLY MONITORING RESIDUE IN MICRO FEATURES

(75) Inventors: Bert M. Vermeire, Phoenix, AZ (US); Farhang F. Shadman, Tucson, AZ (US)

(73) Assignee: Environmental Metrology Corporation, Tucson, AZ (US)

( * ) Notice: Subject to any disclaimer, the term of this patent is extended or adjusted under 35 U.S.C. 154(b) by 0 days.

(21) Appl. No.: 11/205,635

(22) Filed: Aug. 16, 2005

Related U.S. Application Data

(60) Provisional application No. 60/624,131, filed on Nov. 2, 2004.

(51) Int. Cl.
*G01R 27/28* (2006.01)
*G01R 27/04* (2006.01)

(52) U.S. Cl. ................ 324/627; 324/629; 324/628

(58) Field of Classification Search ........... 324/627, 324/629, 628
See application file for complete search history.

(56) References Cited

U.S. PATENT DOCUMENTS

| | | | | |
|---|---|---|---|---|
| 5,861,754 A | * | 1/1999 | Ueno et al. | 324/660 |
| 6,145,384 A | * | 11/2000 | Ikeda et al. | 73/780 |
| 6,903,918 B1 | * | 6/2005 | Brennan | 361/306.1 |
| 2004/0245580 A1 | * | 12/2004 | Lin | 257/379 |

OTHER PUBLICATIONS

K. Romero et al "In-situ analysis of wafer surface and deep trench rinse," Cleaning Technology in Semiconductor Device Manufacturing VI, The Electrochemical Society, 2000.
A.D. Hebda et al, "Fundamentals of UPW rinse: analysis of chemical removal from flat and patterned wafer surfaces" Cleaning Technology in Semiconductor Device Manufacturing VI, The Electrochemical Society, 2000.
J.Yan et al. "Test Structures for Analyzing Mechanisms of Wafer Chemical Contaminant Removal", IEEE International Conference on Microelectronic Test Structures, pp. 209-213, Mar. 2003.

* cited by examiner

*Primary Examiner*—Anjan Deb
*Assistant Examiner*—Amy He
(74) *Attorney, Agent, or Firm*—Eric A. Gifford

(57) ABSTRACT

The micro sensor is fabricated with a guard that shields the electrodes from the surrounding environment, thereby reducing loss of measurement signal through the parasitic capacitances to the substrate and fluid. The guards are low impedance points in the circuit that are biased to track as closely as possible the ac voltages of the respective electrodes. Each guard is suitably connected to the output of a guard buffer that supplies the current required to ensure that the guard is at all times at nearly the same voltage as the electrode it is guarding. The micro sensor has an improved signal to noise ratio (SNR) over an extended measurement frequency range (bandwidth) for monitoring in-situ the cleaning and drying processes for high aspect ratio micro features in dielectric films oriented perpendicular to the fluid-solid interface during the manufacture of ICs, MEMS and other micro-devices.

19 Claims, 17 Drawing Sheets

SHIELDED MICRO SENSOR AND METHOD FOR ELECTROCHEMICALLY MONITORING RESIDUE IN MICRO FEATURES

CROSS-REFERENCE TO RELATED APPLICATIONS

This application claims benefit of priority under 35 U.S.C. 119(e) to U.S. Provisional Application No. 60/624,131 entitled "Method For Impedance Monitoring Of Fluids And Gases In High Aspect Ratio Structures And Method For Manufacturing Such A Monitor" filed on Nov. 2, 2004, the entire contents of which are incorporated by reference.

BACKGROUND OF THE INVENTION

1. Field of the Invention

This invention relates to monitoring the cleaning and drying processes during the manufacture of ICs, MEMS and other micro-devices and more specifically to a micro sensor for high aspect ratio micro features in dielectric films oriented perpendicular to the fluid-solid interface.

2. Description of the Related Art

A major challenge in manufacturing of the micro and nano devices is the cleaning and drying of very small void features ("micro features"), particularly those with large aspect ratios. These micro features are fabricated in various processing steps and can be very small voids such as gaps, holes, vias or trenches that are intentionally etched. The micro features can also be pores (voids) in a deposited dielectric material. Cleaning and drying occur repeatedly during the processing chain and are, responsible for a significant part of the total processing time and for the consumption of much of the water, chemicals and energy.

In semiconductor manufacturing, trenches and vias are fabricated both in the device level and in the interconnect level. Most of these features have high aspect ratios with submicron openings that are oriented perpendicular to the fluid-solid interface of the device to the cleaning fluid and because of their high aspect ratio and very small width are very difficult to clean and dry. In Integrated Circuits, MEMS and other micro device manufacturing, well controlled cleaning and drying are essential to avoid deformation of layers and improper adhesion of moving parts. Improper cleaning and drying would have a significant effect on manufacturing yield and device performance and reliability in both semiconductor and MEMS fabrication. Over-cleaning, over-rinsing or over-drying results in excessive use of chemicals, water and energy and also increases cycle time and potentially causes yield loss. Therefore, there is a strong economic and environmental incentive to use a process that is "just good enough".

The fine structures left behind after processes such as etching, deposition, and patterning, need to be cleaned and the reaction by-products need to be removed often down to trace levels. This usually involves three steps: 1) application of a cleaning solution; 2) rinsing and/or purging using ultra pure water or other rinsing solutions; and 3) drying by removing and purging the traces of any solvents used during rinsing. Due to the undesirable surface tension associated with aqueous chemicals and non-wetting nature of most future dielectrics, industry is pursing the development of processes based on supercritical fluids such as supercritical carbon dioxide for cleaning and pattern development. Measurement of cleanliness under these processing conditions is very critical.

Cleaning, rinsing, and subsequent drying processes are often performed and controlled almost "blindly" and based on trial and error or past experience. The way these processes are monitored and controlled presently is based on ex-situ testing of wafer, chips, or structures. Within the process tool, fixed recipes are provided by tools and process suppliers. Run-by-run adjustments or control are based on external and delayed information on product performance or product yields. The key reason for this inefficient and costly approach is that no sensors or techniques are available to measure the cleanliness and monitor the removal of impurities from micro features—to measure cleanliness where it actually counts. The sensors that are currently available are used in the fabs to monitor the conditions of fluid inside the process vessels and tanks, but far away from the inside of micro features (that is what needs to be monitored; it is also the bottleneck of cleaning and drying). The present monitoring techniques and devices do not provide realistic and accurate information on the cleanliness and condition of micro features.

Industry currently works around this problem while waiting for a solution; the process condition and cleaning and drying are often set with very large factors of safety (over-cleaning and over-rinsing). Large quantities of water and other chemicals are used (much more than what is really needed). This results in wasted chemicals, increased process time, lowered throughput, increased cost, and it causes reliability issues because of lack of process control.

K. Romero et al "In-situ analysis of wafer surface and deep trench rinse," Cleaning Technology in Semiconductor Device Manufacturing VI, The Electrochemical Society, 2000 propose a trench device for monitoring the process in-situ. As shown in FIG. 1a, a trench device 10 comprises a pair of conducting electrodes (Poly-Si) 12 and 13 sandwiched between dielectric ($SiO_2$) layers 16 and 17 on opposite sides of a trench 14 on a substrate 18. Trench 14 is oriented perpendicular to the fluid-solid interface 19 of the device. An impedance analyzer 20 applies a measurement signal (voltage and current) 21 to the electrodes, which carry the measurement signal to the trench. The impedance analyzer measures the impedance between its two terminals (the impedance consists of the ratio of the voltage and current and the phase difference between the voltage and current).

The electrical equivalent circuit diagram of trench device 10 is presented in FIG. 1b. The sensor is configured to measure the solution resistance $R_{sol'n}$ 22, which is dependent on the ionic concentration of impurities in the fluid 23 inside the trench 14. At solid-solution interfaces, an interface double layer forms because charges in the solution that are mobile (ions) respond to the presence of fixed charges on the solid. The interface double layer is responsible for a capacitance $C_{dl}$ 24 between the electrode and the solution, which forms an impedance $Z_{dl}=1/j\omega C_{dl}$ where $\omega$ is the measurement signal radial frequency. The impedance is in series with $R_{sol'n}$.

Since the sensor measures the solution resistance through two series capacitors, the measurement must be performed using an ac signal. If the series impedance $Z_{dl}$ is much larger than $R_{sol'n}$, (i.e. if $C_{dl}$ is small and/or the measurement radial frequency $\omega$ is small so that $R_{sol'n} \ll 1/j\omega C_{dl}$), then the sensor's impedance output is dominated by $C_{dl}$ and the solution resistance $R_{sol'n}$ can not be effectively measured.

The electrodes also form parasitic capacitances with other conductors in their neighborhood. The total parasitic capacitance is primarily between the electrodes 12 and 13 and the substrate 18 represented by capacitors $C_{substrate}$ 26 and 27.

There can also be significant capacitance between the electrode and the fluid above the electrode, and this is represented by the capacitors $C_{fluid}$ 28 and 29. The parasitic capacitances form parasitic shunt circuits across the solution resistance. These shunt circuits are in parallel with the solution resistance and therefore allow the measurement signal 21 to bypass the solution resistance. If the shunt circuit impedance is significantly lower than the solution resistance, then the sensor's impedance output is dominated by the parasitic capacitances and the solution resistance can not be effectively measured.

For the sensor to be useful as a monitor of the fluid in the micro feature, the total parasitic capacitance must be sufficiently small to allow an electrical measurement of the total impedance between the electrodes to resolve $R_{sol'n}$ and/or $C_{dl}$. If the parasitic capacitance dominates the total electrical response, then the circuit will not have a good signal to noise ratio and the sensor will not be very sensitive. In the paper by Romero et al., the parasitic capacitance was found to dominate the solution resistance. At the parasitic capacitance measured (88 pF), the equivalent circuit calculation predicts no discernable impedance variation between highest and lowest trench resistances. The full ionic concentration range was not experimentally resolvable in comparison to electronic noise. Despite the difficulties encountered, a trench resistivity device still holds promise in resolving the process chemical evolution out of a sub-micron trench.

SUMMARY OF THE INVENTION

The present invention provides a micro sensor having an improved signal to noise ratio (SNR)-over an extended measurement frequency range (bandwidth) for monitoring the cleaning and drying processes for micro features in dielectric films during the manufacture of ICs, MEMS and other micro-devices, and more particularly for high aspect ratio micro features in dielectric films having openings in the plane of the sensor fluid-solid interface and which are ordinarily oriented perpendicular to the fluid-solid interface.

This is accomplished by providing each electrode with a guard that shields the electrode from the surrounding environment and thereby reduces the loss of signal through the parasitic capacitances to the substrate and fluid. The guards are low impedance points in the circuit that are biased to track as closely as possible the AC voltage of the respective electrodes. Each guard is suitably connected to the output of a guard buffer that supplies the current required to ensure that the guard is at all times at nearly the same voltage as the electrode it is guarding. The guards are suitably configured to surround the electrodes (above, below and sides) except at the edges of the trench and at the electrode contacts. However, in certain micro sensor configurations it may be sufficient for the guard to only partially surround the electrodes, e.g. above and below or just above.

The voltage difference between the electrode and its guard is several orders of magnitude lower than the voltage difference between the electrode and other conductors e.g. substrate and fluid, that are part of the sensor or are in the neighborhood of the sensor. Therefore, the loss or distortion of the measurement signal through the parasitic capacitance will be very, very small. This guarding has the effect of shifting the high frequency cutoff limit of the measurement to much higher frequencies. Consequently, the low frequency cutoff limit can also be allowed to shift to higher frequencies, which means capacitance $C_{dl}$ can be smaller, hence the entire micro sensor can be made smaller. A smaller micro sensor is critical to in-situ monitoring because the manufacturing cost of the sensor can be lower. Because the guards render the parasitic capacitance irrelevant, thinner dielectric films (which would cause larger parasitic capacitance if no guard is used) can be used in the sensor, hence standard foundry processes can be used to manufacture the sensor.

In addition, the guards shield the sensor from environmental noise thereby improving the signal to noise ratio. The signal to noise ratio of the micro sensor without the guard is determined by the geometry of the sensor, the materials choice and the ambient noise. The signal to noise ratio of the micro sensor with the guard is not determined by the parasitic elements, but by the accuracy of the electronics used to measure the trench impedance.

These and other features and advantages of the invention will be apparent to those skilled in the art from the following detailed description of preferred embodiments, taken together with the accompanying drawings, in which:

DETAILED DESCRIPTION OF THE INVENTION

The present invention provides a micro sensor having an improved SNR over an extended bandwidth for monitoring the cleaning and drying processes for high aspect ratio features in dielectric films with an opening in the plane of the fluid-solid interface during the manufacture of ICs, MEMS and other micro devices. Typical dielectric films include silicon dioxide ($SiO_2$), silicon nitride ($Si_3N_4$), high-K dielectric materials ($TiO_2$) and low-K organic materials commonly used in the microelectronics manufacturing process. All high aspect ratio void structures with an opening in the plane of the fluid-solid interface such as trenches, vias, holes, pores, etc. will be generally referred to as a "micro feature" hereafter. While in principle the micro feature can be tilted relative to the fluid-solid interface, such micro features are generally oriented substantially perpendicular to the fluid-solid interface and also perpendicular to the substrate on which they are built. The micro feature may deviate from perpendicular or exhibit a slightly tapered etch profile due to standard etching or milling processes. The micro feature may be filled with a porous dielectric material as well. These void micro features have aspect ratios of greater than 1:1, typically at least 3:1 and potentially much larger.

Figure 1A:
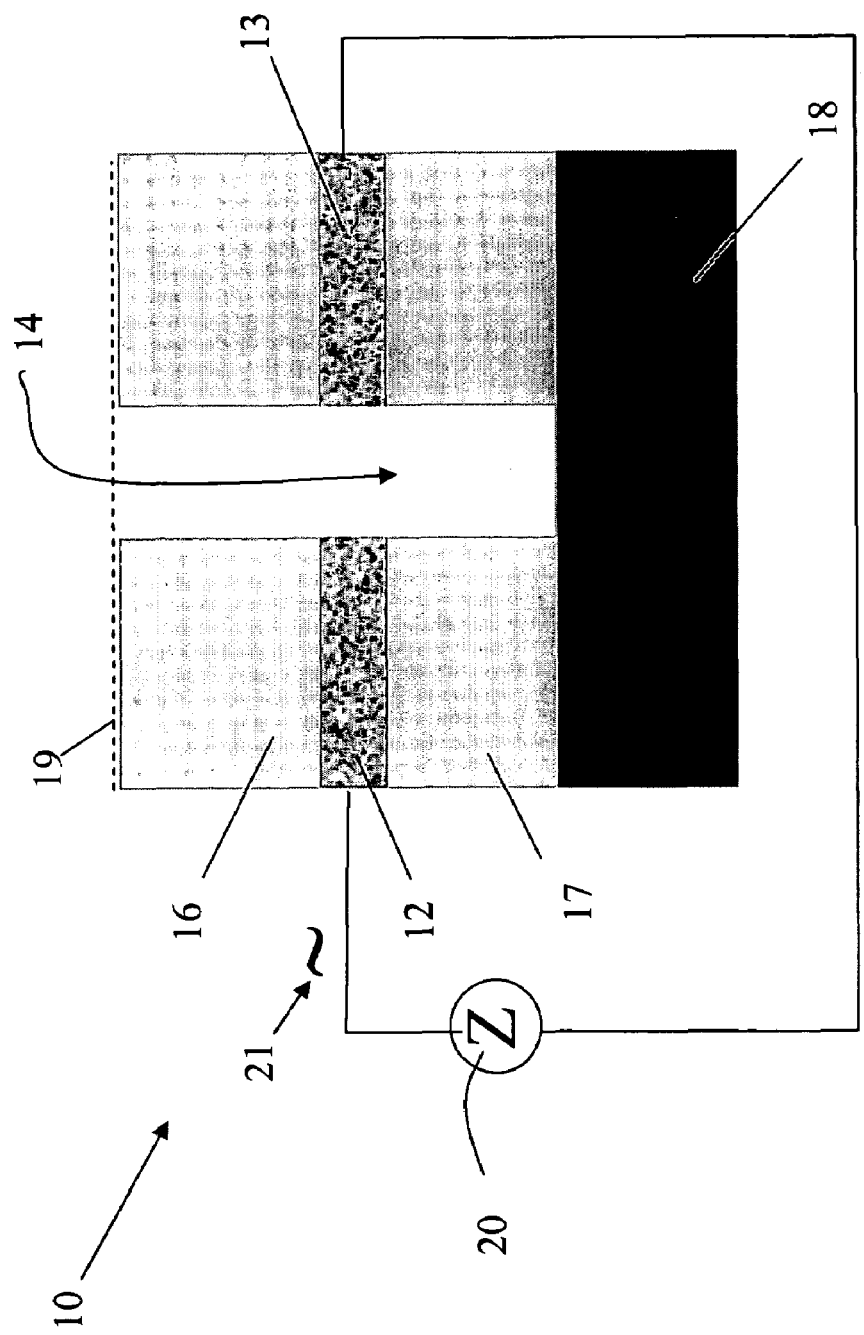
FIGS. 1a and 1b, as described above, are a section view of a known micro sensor for high aspect ratio structures in dielectric films and its equivalent circuit.
Figure 1B:
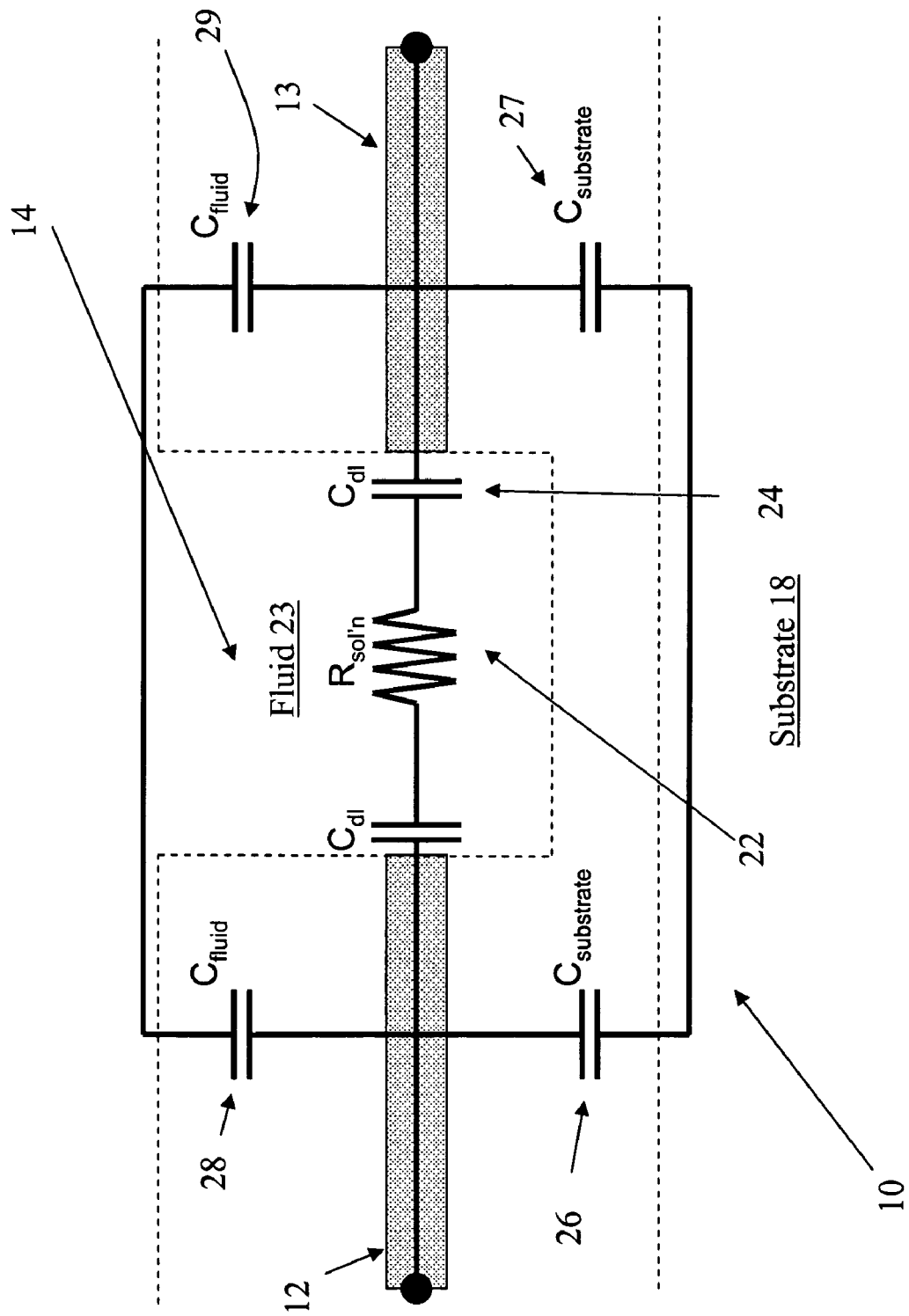
Figure 2:
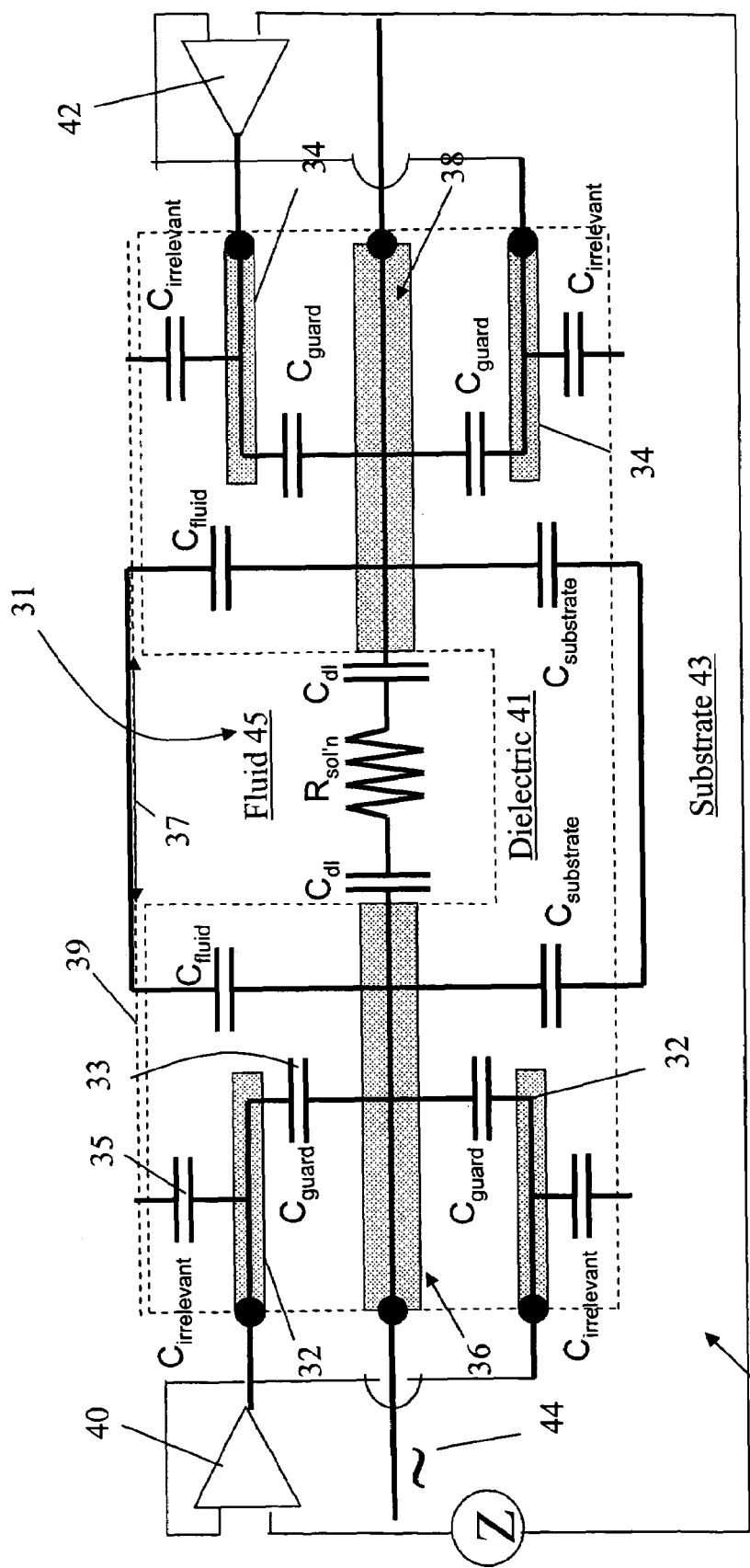
FIG. 2 is an equivalent circuit of a micro sensor including a guard in accordance with the present invention.

As shown in FIG. 2, the equivalent circuit of a micro sensor 30 in accordance with the present invention for monitoring a micro feature 31 having an opening 37 in the plane of the fluid-solid interface 39. Micro sensor 30 includes guards 32 and 34 that shield electrodes 36 and 38, respectively. A guard is an additional conductor that divides the dielectric 41 between an electrode and the substrate 43 and/or the electrode and the fluid 45 into two parts, and so form two new capacitors, $C_{guard}$ 33 and $C_{irrelevant}$ 35. $C_{guard}$ is the capacitor between the electrode and the guard. $C_{irrelevant}$ is the capacitor between the guard and the substrate and/or the guard and the fluid.

The guards are biased so that their voltages follow as closely as possible the respective electrode voltages at all times, even when the electrode voltage changes over time. The guard voltage need only track the ac component of the electrode voltage but suitably tracks the total instantaneous electrode voltage. The current required to make the guard voltage the same as the electrode voltage is supplied by buffers 40 and 42, e.g. an operation amplifier (OpAmp), not by the measurement signal 44. The Buffer reproduces the desired voltage without significant loading it. Since the voltage difference between the electrode and its guard is several orders of magnitude lower than the voltage difference between the electrode and other conductors in the neighborhood of the sensor (substrate and fluid), the loss or distortion of the measurement signal through the parasitic capacitance $C_{guard}$ will be very, very small. The measurement signal is not affected by the capacitor $C_{irrelevant}$ because the measurement signal is buffered prior to being applied to the guard. $C_{irrelevant}$ must be charged and discharged by the guard buffer.

Figure 3:
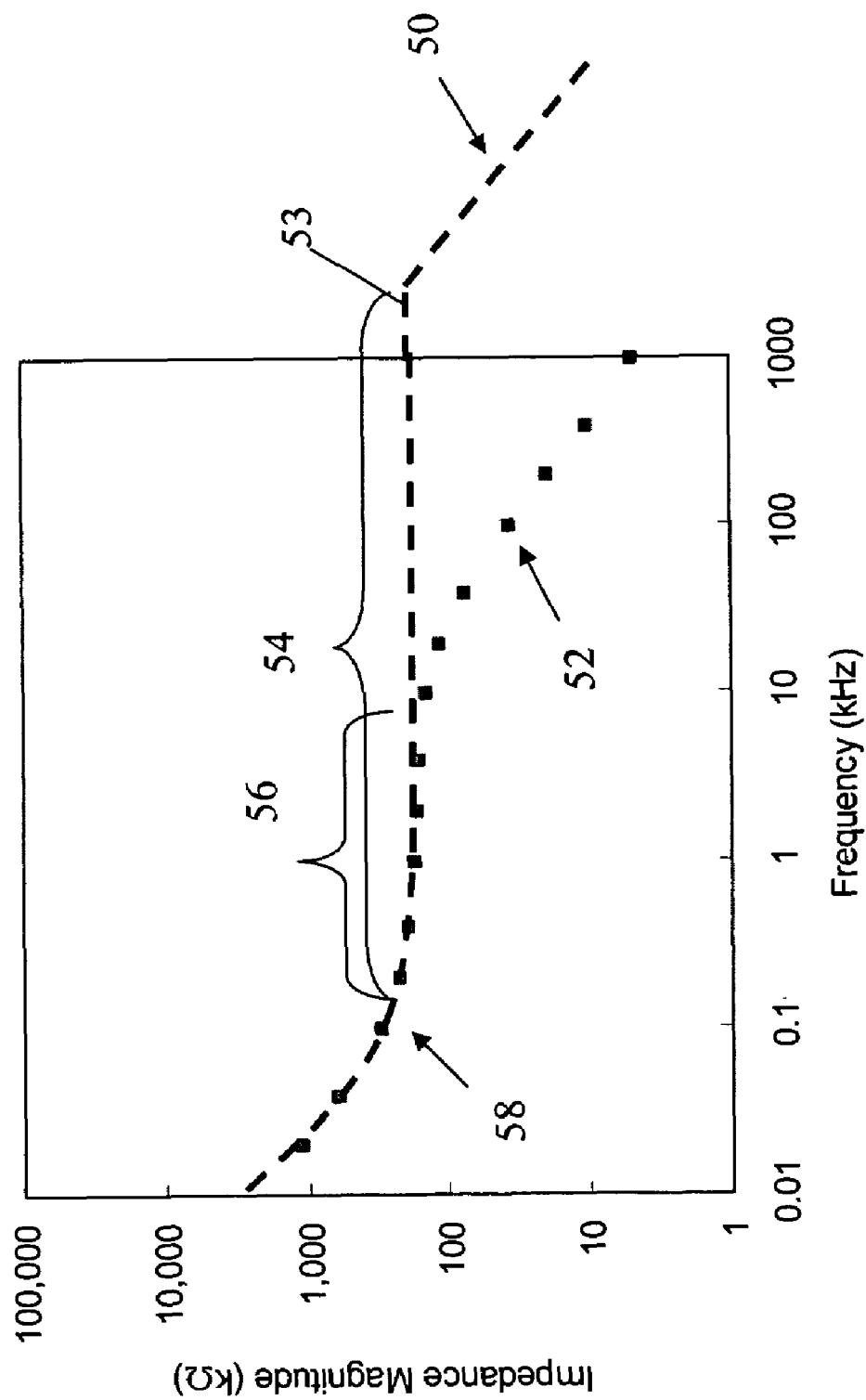
FIG. 3 is a calibration plot of impedance vs. frequency for the micro sensors illustrating the frequency extension achieved by the present invention.

FIG. 3 is a plot of the micro sensor's frequency response with a guard 50 and without a guard 52. With a guard the loss or distortion of the measurement signal through the parasitic capacitance $C_{parasitic}$ will be very, very small. This makes the effective impedance of the shunt path (the path the signal must take to bypass the micro feature) that limits the high frequency operation much larger. The net effect is to shift the high frequency limit 53 of the measurement to much higher frequencies so that the useful measurement region 54 with a guard is much wider than the useful measurement region 56 without a guard. The smaller the fraction of the electrode that is covered by the guard, the lower the frequency 53 that high frequency roll-off will occur.

It is desirable to make the electrode as small as possible to reduce the sensor's manufacturing cost. The frequency at which low frequency roll-off occurs 58 is determined by the capacitance $C_{dl}$ and resistance $R_{sol'n}$. In the absence of a guard, the frequency at which high frequency roll-off occurs 52 is determined by the total parasitic capacitance (the sum of the capacitance between the electrode and the substrate and between the electrode and the fluid) and the resistance $R_{sol'n}$. Reducing the active electrode area (area of the electrode that is exposed to the fluid inside the micro feature) reduces $C_{dl}$, which increases the frequency at which low frequency roll-off occurs. In the absence of a guard, reducing the electrode active area does not increase the frequency at which high frequency roll-off occurs as much as the low frequency roll-off. Hence reduction of the electrode active area will tend to bring the low frequency roll-off and the high frequency roll-off closer together. If the electrode active area is reduced too much (causing the high frequency roll-off and low frequency roll-off to overlap), accurate measurement of $R_{sol'n}$ is no longer possible. Hence reducing the size of the electrode is limited if there is no guard. A guard allows the high-frequency roll-off to be extended to higher frequencies without penalty to the low frequency roll-off. The low frequency roll-off can therefore be allowed to increase in frequency by reducing the size of the sensor.

The signal to noise ratio of the micro sensor without the guard is determined by the geometry of the sensor and the materials choice. The signal to noise ratio of the micro sensor with the guard is not determined by the parasitic elements, but by the accuracy of the electronics used to measure the trench impedance. The micro sensor with guard can therefore measure the micro feature impedance more accurately in a noisier environment.

Figure 4A:
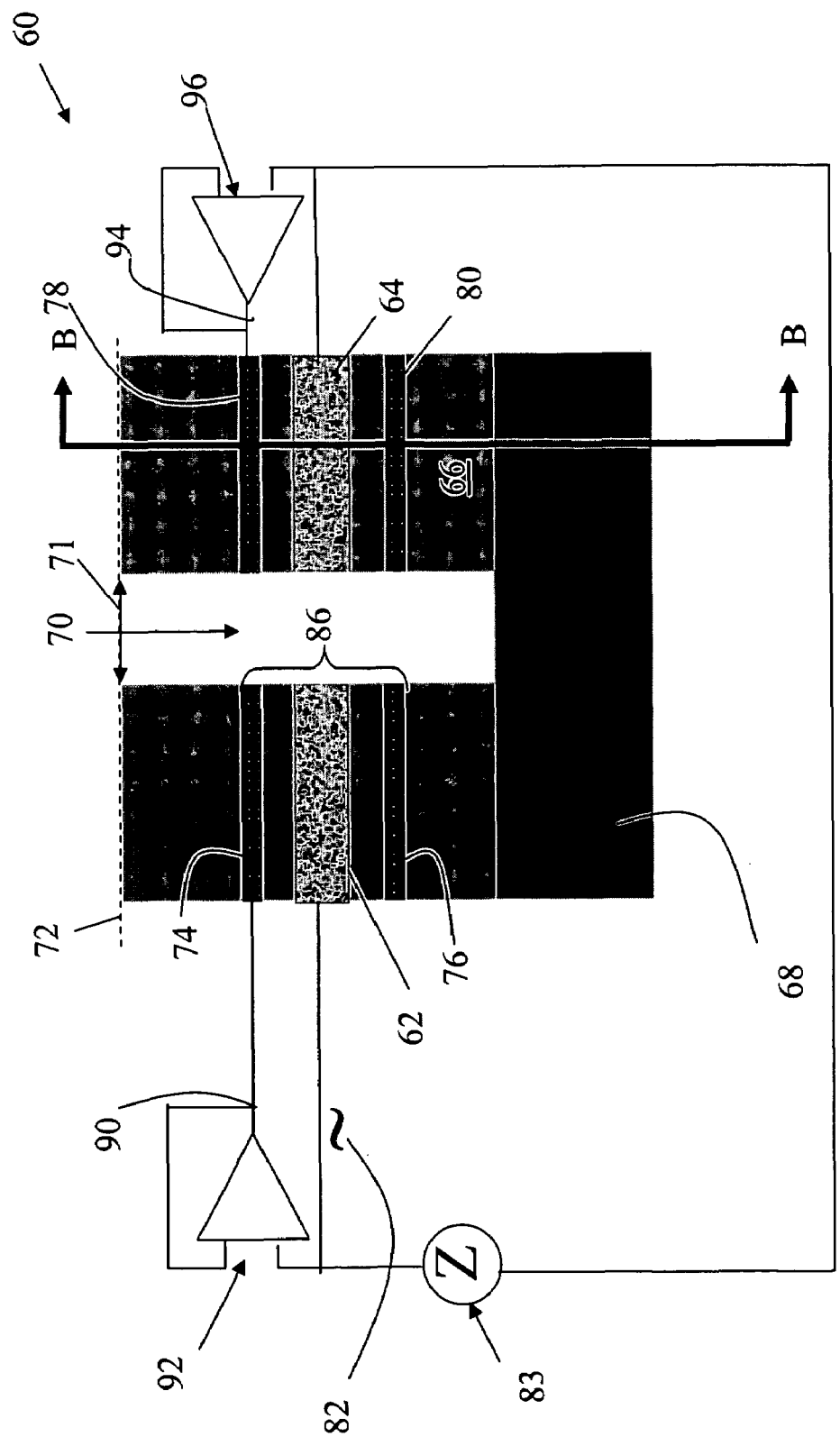
FIGS. 4a and 4b are section and plan views of an embodiment of the micro sensor in which the guard surrounds the electrodes except at the electrode contact and at the micro feature.
Figure 4B:
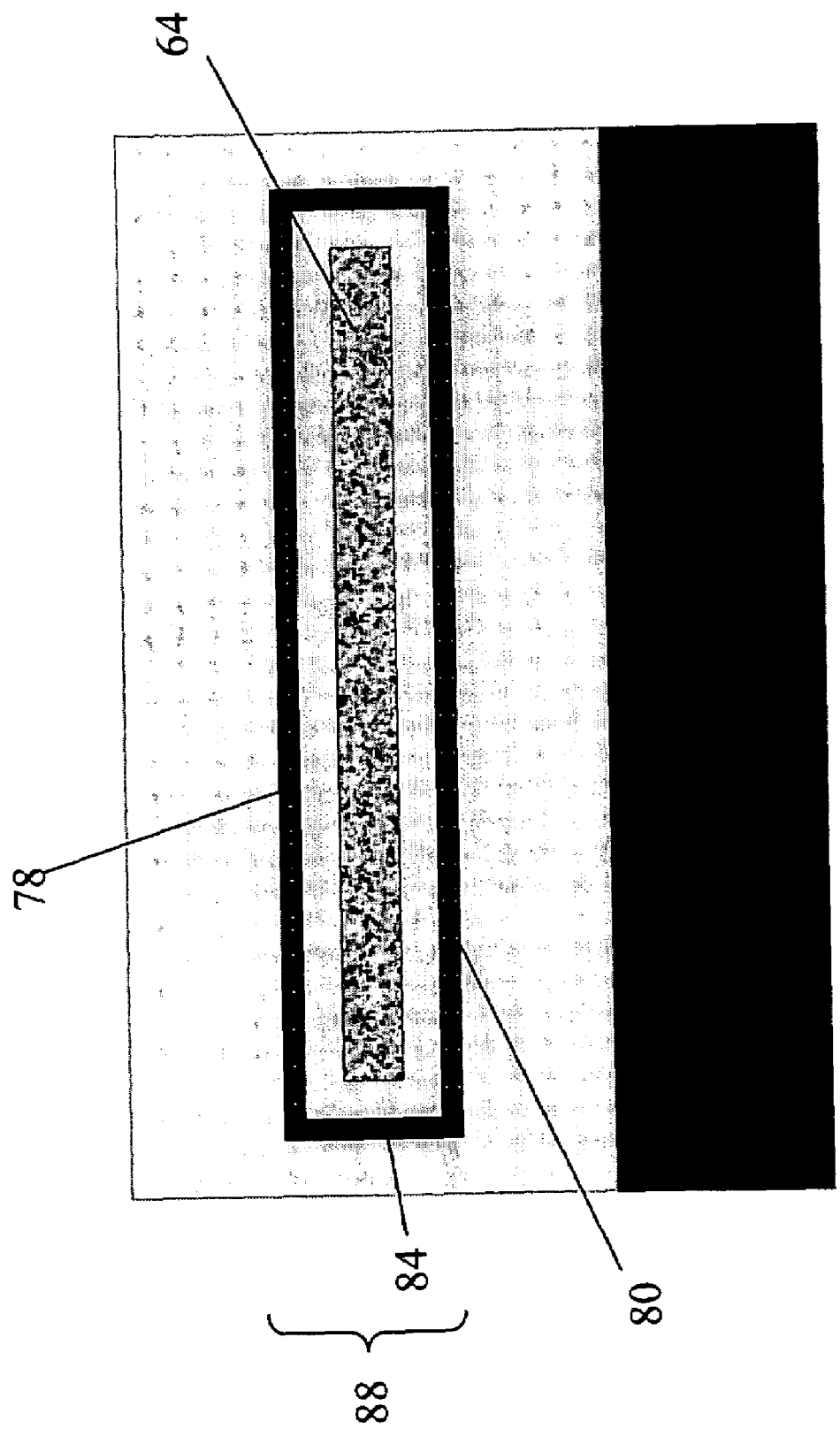
Figure 5:
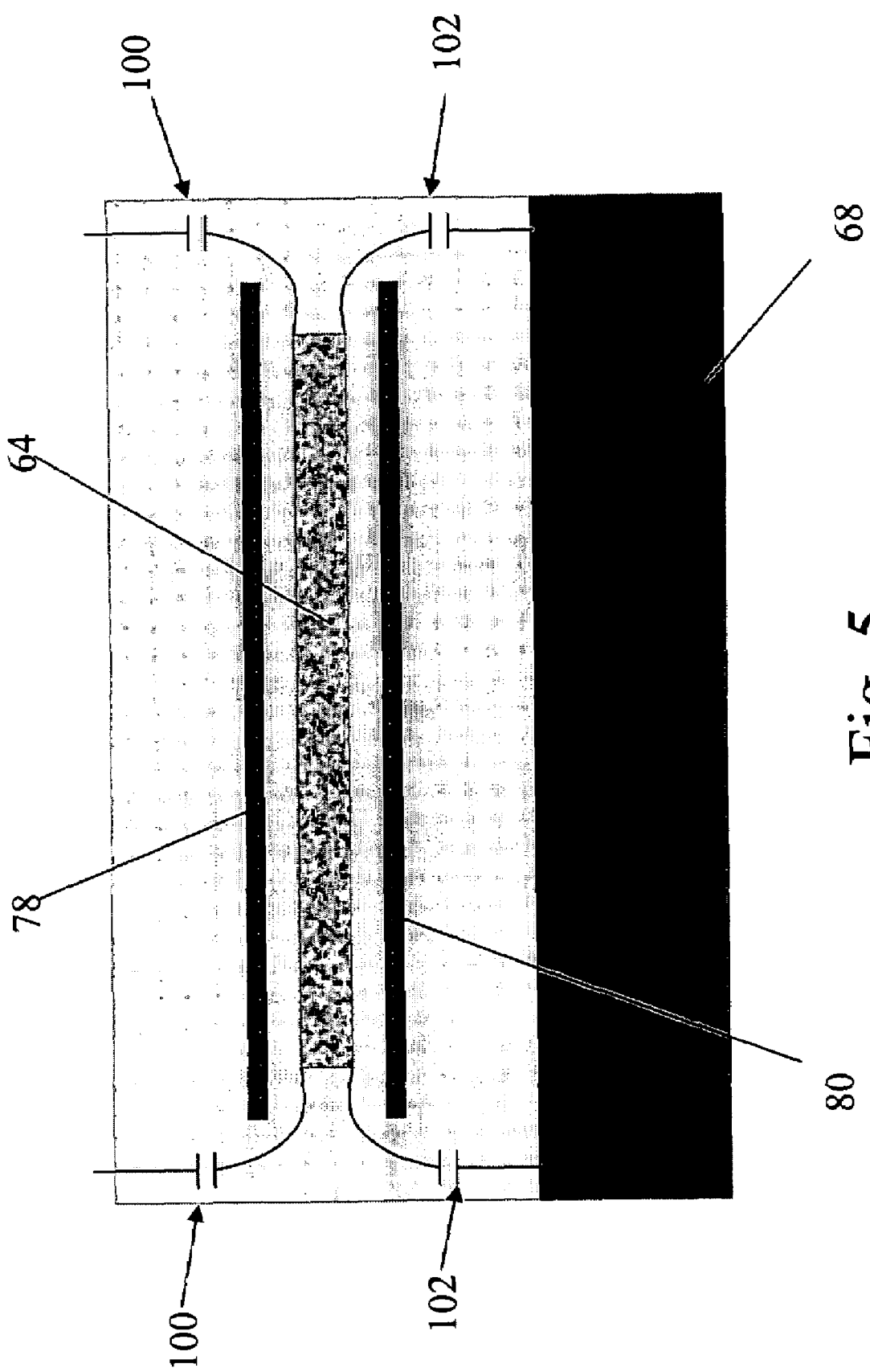
FIG. 5 is a section view of another embodiment of the micro sensor in which the guard is placed above and below the electrodes.
Figure 6:
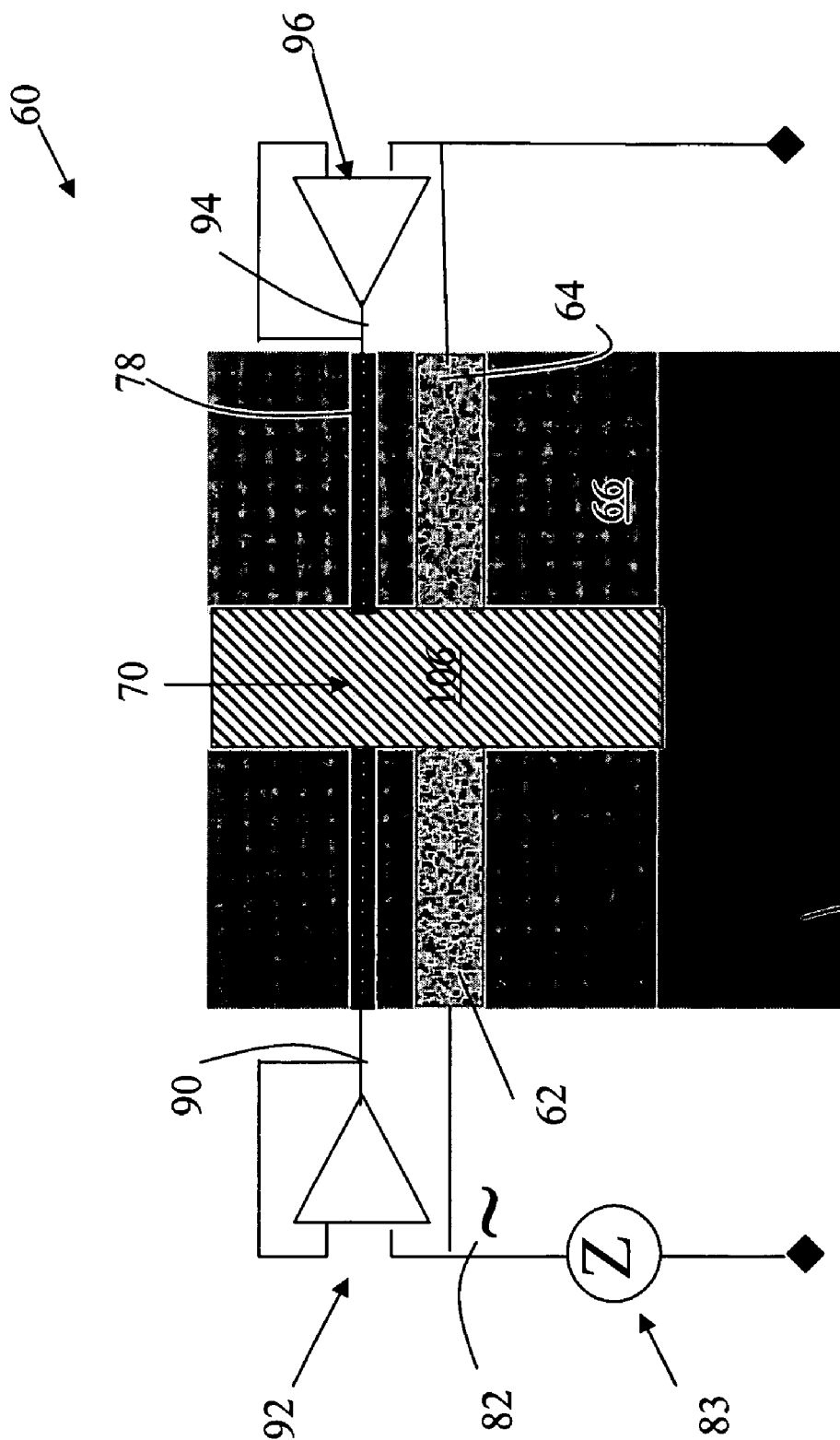
FIG. 6 is a section view of another embodiment of the micro sensor in which the guard is only placed above the electrodes and the micro feature is filled with a porous dielectric.

Ideally the guard is configured to completely surround (above, below and sides) the electrodes except at the edges of the trench and at the electrode contacts as shown in FIGS. 4a and 4b. However, in certain micro sensor configurations it may be sufficient for the guard to only partially surround the electrodes as shown in FIGS. 5 and 6.

As shown in FIGS. 4a and 4b, a micro sensor 60 includes a pair of electrodes 62 and 64 in a dielectric 66 on a substrate 68 on either side of a micro feature 70 having an opening 71 that lies in the plane of the fluid-solid interface 72. As shown, the micro feature is suitably oriented substantially perpendicular to the fluid-solid interface 72 and the dielectric stack. Conductive layers 74,76 and 78,80 lie above and below electrodes 62 and 64, respectively, on either side of micro feature 70 and the conductors (not shown) that carry the measurement signal 82, which is supplied by the impedance analyzer 83 to the electrodes (such as a coaxial cable). A conductive perimeter 84 on either side of electrode 62 electrically connects layers 74 and 76 to form a guard 86. Similarly the conductive perimeter 84 on either side of electrode 64 electrically connects layers 78 and 80 to form a guard 88. The guards effectively surround their electrodes except at the edges of the micro feature and at the electrode contacts and electrically shield the electrodes from the surrounding environment.

The guard 86 is suitably connected to the output 90 of a guard buffer 92 that ensures that the guard is always at nearly the same voltage as electrode 62. Similarly, guard 88 is suitably connected to the output 94 of a guard buffer 96 that ensures that the guard is always at nearly the same voltage as electrode 64. The guards are only used to shield the electrodes from the rest of the environment and do not otherwise contribute to the measurement. The current required to make the guard voltage the same as the electrode voltage is supplied by buffers 92 and 96, not by the impedance analyzer 83, hence it does not distort the measurement signal 82.

The AC measurement signal 82 is applied between the two electrodes 62 and 64 and the impedance is measured by the impedance analyzer 83 as the ratio and phase difference between the measurement signal voltage and current. During monitoring, the change in monitor impedance is an indication of chemical removal/addition from the micro feature 70 or of motion of a chemical species inside the micro feature. The measured device impedance is related to the concentration inside the micro feature or to the surface concentration inside the pores of the dielectric film 66, thereby producing a concentration-versus-time profile. With the inclusion of the guard, the effective parasitic capacitance is sufficiently small to allow an electrical measurement of the total impedance between the electrodes to resolve $R_{sol'n}$ and/or $C_{dl}$.

As mentioned previously, the guards do not necessarily need to completely surround the electrodes. As shown in FIG. 5, it may be sufficient for guards to include only conductive layers 78,80 that lie above and below the electrodes 64 (no conductive perimeter). This is allowable if the sidewall fringing capacitance 100 to the fluid and the sidewall fringing capacitance 102 to the substrate are small relative to the other equivalent circuit elements. These capacitances will be small if the electrode 64 is thin and flat and/or if the above 78 and below 80 guard layers extend beyond the electrode 64.

As shown in FIG. 6, if the dielectric 66 to the substrate 68 is very thick, then the substrate capacitance is very small. This could be the case if glass is used as a substrate. If the substrate capacitance $C_{substrate}$ is very small, then the underlying conductive layer portions 76, 80 and sidewall portion 84 of the guards are not required. As shown in this particular embodiment, micro feature 70 is filled with a porous material 106. In that case, the pores fill with fluid (i.e. the porous material is soaked) and the sensor's electrical response is indicative of the residual contamination inside the pores of the porous material.

Although described in the context of a micro feature having an opening in the plane of the sensor fluid-solid interface and which is generally oriented perpendicular to that interface, the guard electrodes and buffering scheme may be employed to shield micro sensors for monitoring micro channel and surface film micro features as disclosed in copending U.S. patent applications entitled "Micro Sensor and Method for Electrochemically Monitoring Residue in Micro Channels" and "Surface Micro Sensor and Method", respectively, which are hereby incorporated by reference. To generalize, the micro sensor includes a micro feature formed in or on a dielectric and a pair of electrodes formed in or on the dielectric adapted to receive an ac measurement signal to measure the impedance of the micro feature between the electrodes. Buffers supply current to conductive guards formed in the dielectric near the respective electrodes so that their voltages closely track the electrode voltages and shield the electrodes from the surrounding environment, thereby reducing the loss of measurement signal through the parasitic capacitance.

For rinsing applications, the presence of ionic contaminants in ultra pure water changes the resistivity of the water even if very small concentrations (parts per billion level) are present. Therefore, the impedance measured between two electrodes will depend very much on the conductivity of the fluid and thus the presence of ions. Even non-ionic impurities, directly and through interactions with other species present, change the dielectric properties and surface response to ions inside the micro feature, which in turn define the impedance. For drying applications, the removal of the water from the micro feature (replacing it with air, pure nitrogen or some other gas) will likewise result in a measurable change in impedance, since the difference between the conductivity of ultra pure water and air can easily be detected. Conduction along sidewalls can be measured, so that the amount of moisture adsorbed on the sidewalls or (slightly) conducting residual impurities on the sidewalls will be detected.

The micro sensor 30 measures resistivity inside the micro feature, not in the bulk of a fluid. Bulk properties are often irrelevant both in terms of the amount and also the rate of change. This means that the sensor is placed "adjacent to" the micro feature that needs to be monitored for cleaning or drying to monitor the "inside" of the micro feature. The capability to perform in-situ measurements is why it is so important to be able to reduce the size of the micro sensor without sacrificing performance.

Furthermore, micro sensor 30 measures the full impedance spectrum, of which the resistivity is just a part (impedance is a complex number quantity that is dependent on frequency while resistance is the real part of the dc value of the impedance). This means that a large amount of other information, such as the dielectric absorption and frequency dependence is also available. The sensor can monitor specific ionic species and or non-ionic species (since these change the permittivity and surface adsorption). Because trace quantities of impurities can result in significant change in conductance or dielectric constant and because these electrical properties can be accurately measured, the sensitivity of the sensor is very good.

An exemplary process for fabricating a particular micro sensor 60 with a specific micro feature 70 as shown in FIGS. 4a and 4b is illustrated in FIGS. 7a through 7k.

Figures 7A, 7B:
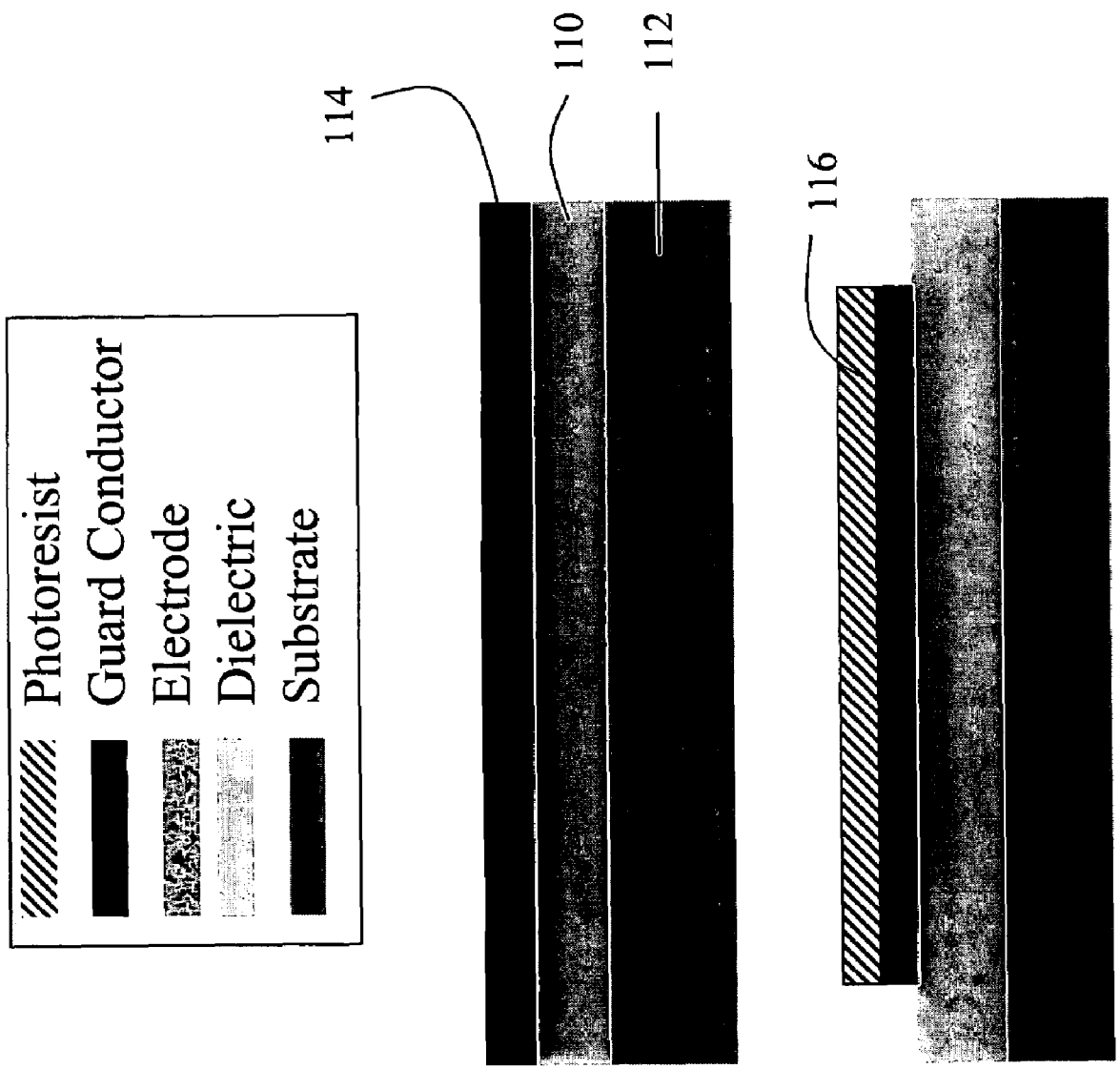
FIGS. 7a through 7k are section views of a process for fabricating the micro sensor shown in FIG. 4.

As shown in FIG. 7a, a dielectric 110 such as $SiO_2$ is deposited with a typical thickness of about 5 μm on a substrate 112, which can be silicon, glass or a similar inert material. Optionally, if the substrate itself is a dielectric such as glass, this step may be omitted. A conductor 114 such as copper or doped polysilicon with typical thickness of 0.5 μm is deposited on dielectric 110 and will form the bottom section of the guard.

As shown in FIG. 7b, a photoresist 116 is deposited on conductor 114 and the pattern of the bottom section of the guard (80 and 76 shown in FIGS. 4a and 4b) is defined using photolithography and chemical etching.

Figure 7C:
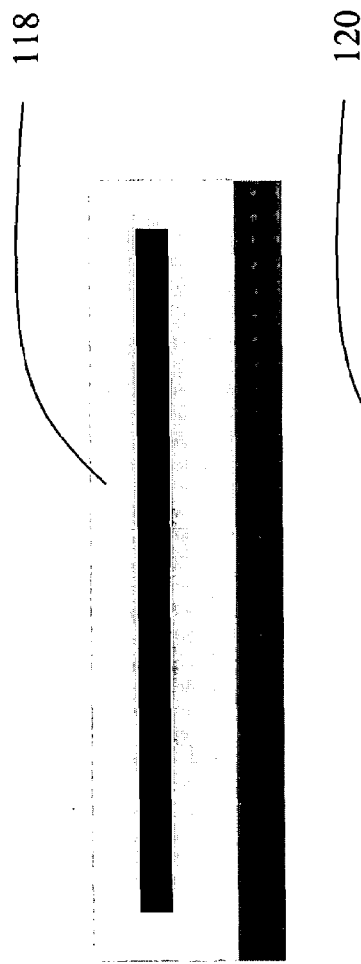

As shown in FIG. 7c, the photoresist is removed and a second dielectric 118, such as $SiO_2$ is deposited with a typical thickness of 2 μm on top of the patterned bottom section of the guard.

Figure 7D:
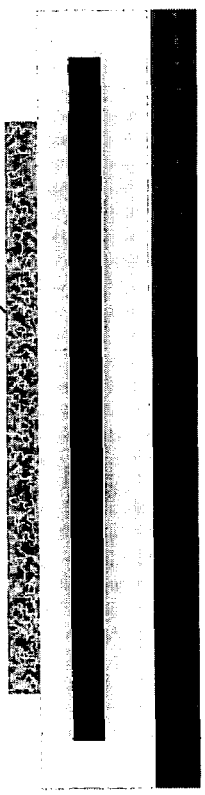

As shown in FIG. 7d, an electrode 120, made of a material such as doped polysilicon, is deposited on the second dielectric with a typical thickness of 1 μm. The electrode is patterned using photoresist deposition, photolithography and chemical etching. The photoresist is then removed.

Figure 7E:
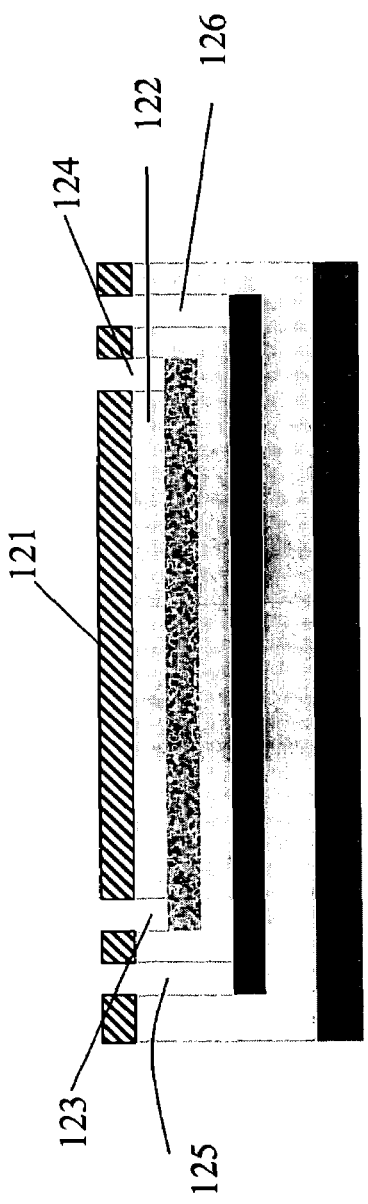

As shown in FIG. 7e, a third dielectric 122, such as $SiO_2$, is deposited on top of the patterned electrode with a typical thickness of 2 μm. A photoresist 121 is deposited on this dielectric and patterned using photolithography to form openings. The dielectric is etched to form vias 125 and 126, where the sidewalls of the guard will be formed (84 in FIG. 4b) and to form vias 123 and 124 where the contacts for the electrode will be formed.

Figure 7F:
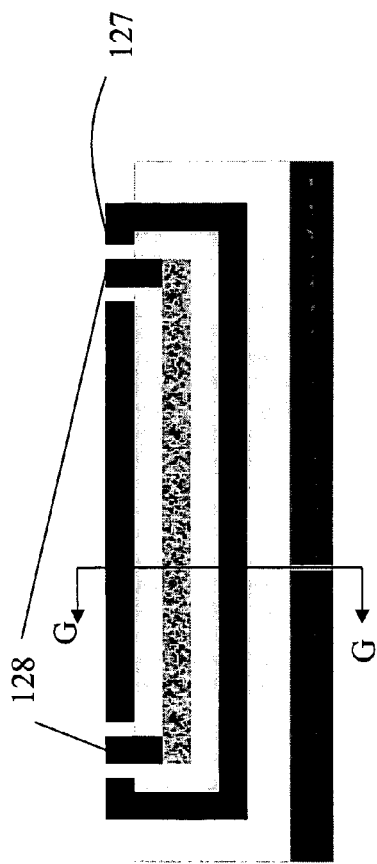
Figure 7G:
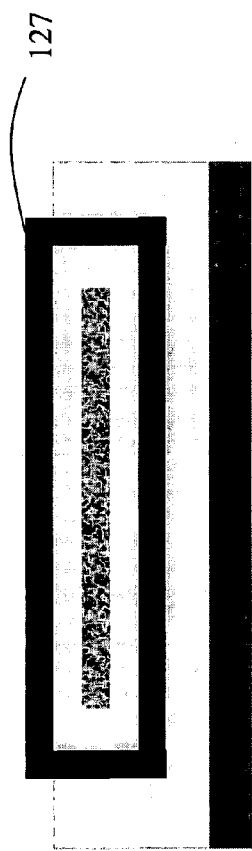

As shown in FIG. 7f, the photoresist is removed and a conductor 127 for the top guard 74,78 is deposited with a typical thickness of 0.5 μm. This process also fills in the sidewalls 84 of the guard and the contacts to the electrode 128. Photoresist is deposited and patterned using photolithography and the top guard (74 and 78 in FIG. 4a and FIG. 4b) is chemically etched. The cross section along section G-G at this point in the fabrication process showing that the electrode is completely surrounded by the guard is shown in FIG. 7g.

Figure 7H:
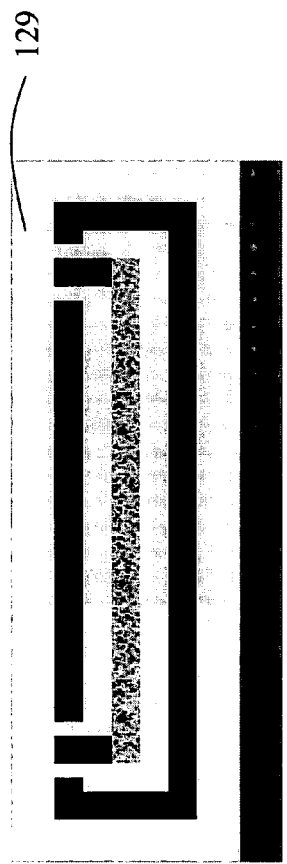

As shown in FIG. 7h, a fourth layer of dielectric 129 such as $SiO_2$ is deposited with a typical thickness of 3 μm.

Figure 7I:
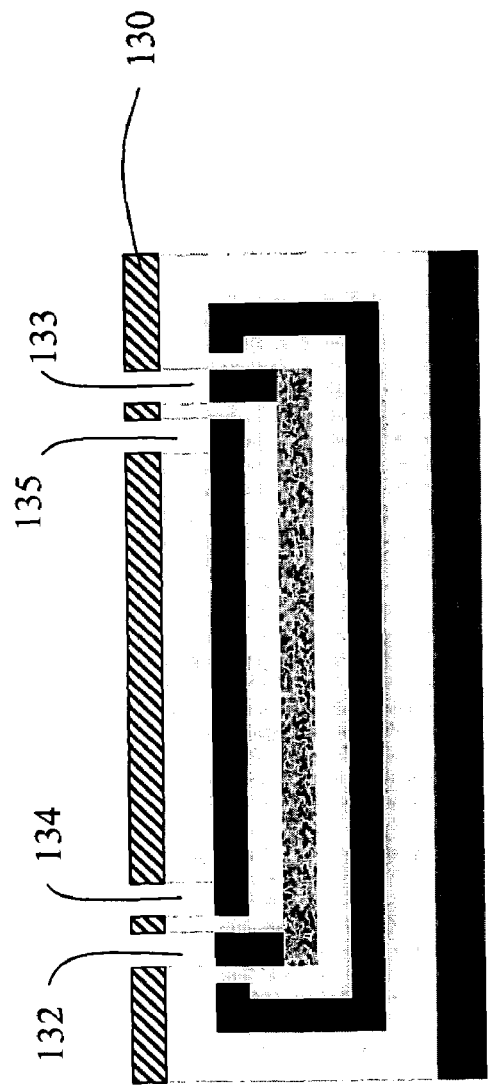

As shown in FIG. 7i, a layer of photoresist 130 is deposited and patterned using photolithography. Contact openings to the electrode contact 132,133 and guard 134,135 are chemically etched.

Figure 7J:
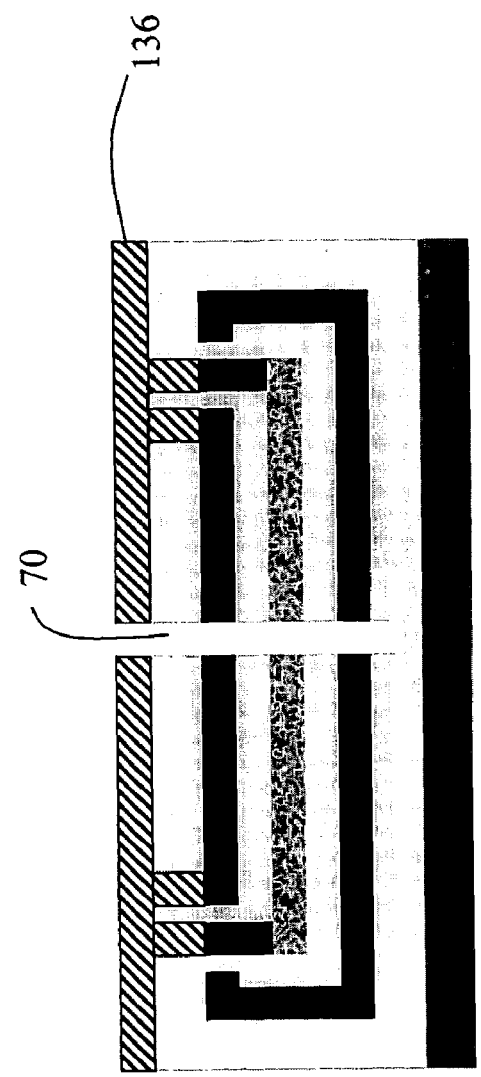

As shown in FIG. 7j, the photoresist is removed and a new layer of photoresist 136 is deposited and patterned using photolithography. The micro feature 70 is then formed by chemical etching. Micro feature 70 has an opening 139 in the plane of the fluid-solid interface and extends through said second dielectric 118 and electrode 120 suitably substantially perpendicular to the stack of dielectric and conductive layers. Micro feature 70 may extend partially or completely through first dielectric 110 as shown in FIG. 7j and possibly into substrate 112. As shown in this embodiment, micro feature 70 extends through both conductive guard layers 114 and 127 as well. Then, photoresist 136 is removed.

Figure 7K:
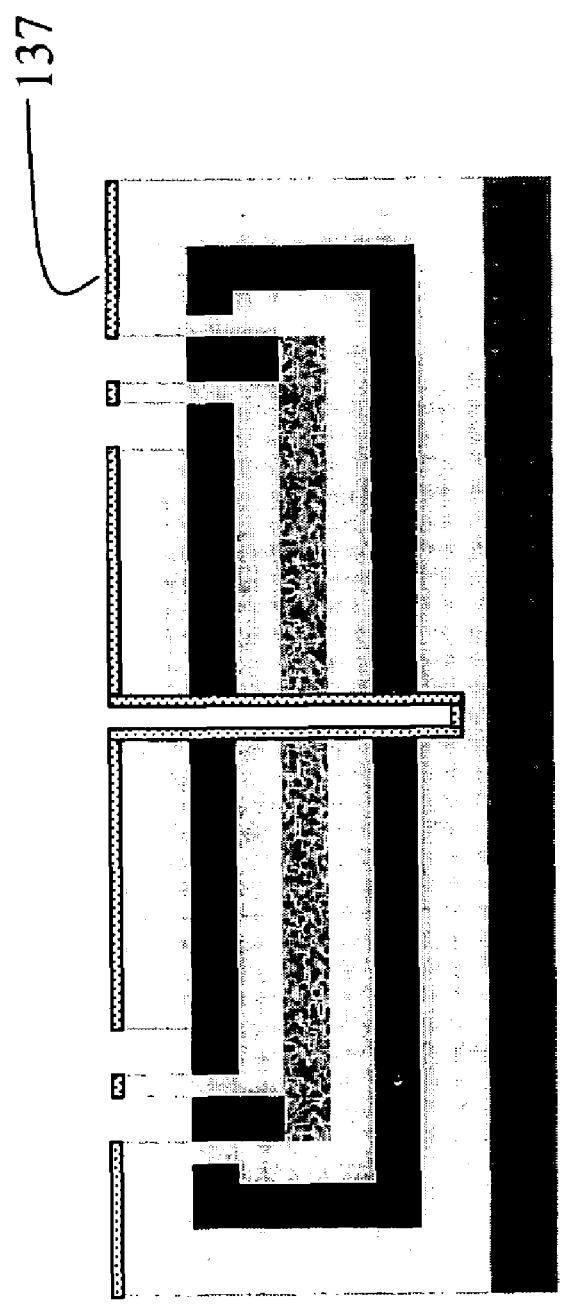

As shown in FIG. 7k, optionally the micro feature can be coated with a covering dielectric 137, such as $SiO_2$ or $TiO_2$ with a typical thickness of 3 nm to 0.3 μm. This covering layer makes the sensor sensitive to the particular dielectric that is used to make the covering level, which may or may not be the same material as the other dielectric layers. The covering layer also has the effect of increasing the aspect ratio of the micro feature. It also reduces the effective value of the double layer capacitance and the parasitic capacitance. If the capping layer is made using a very inert material, it also makes the sensor less sensitive to a corrosive chemical environment. To finish the optional covering process, the contacts are etched free again using a process of deposition of photoresist, photolithography patterning, chemical etching and photoresist removal.

Figure 8:
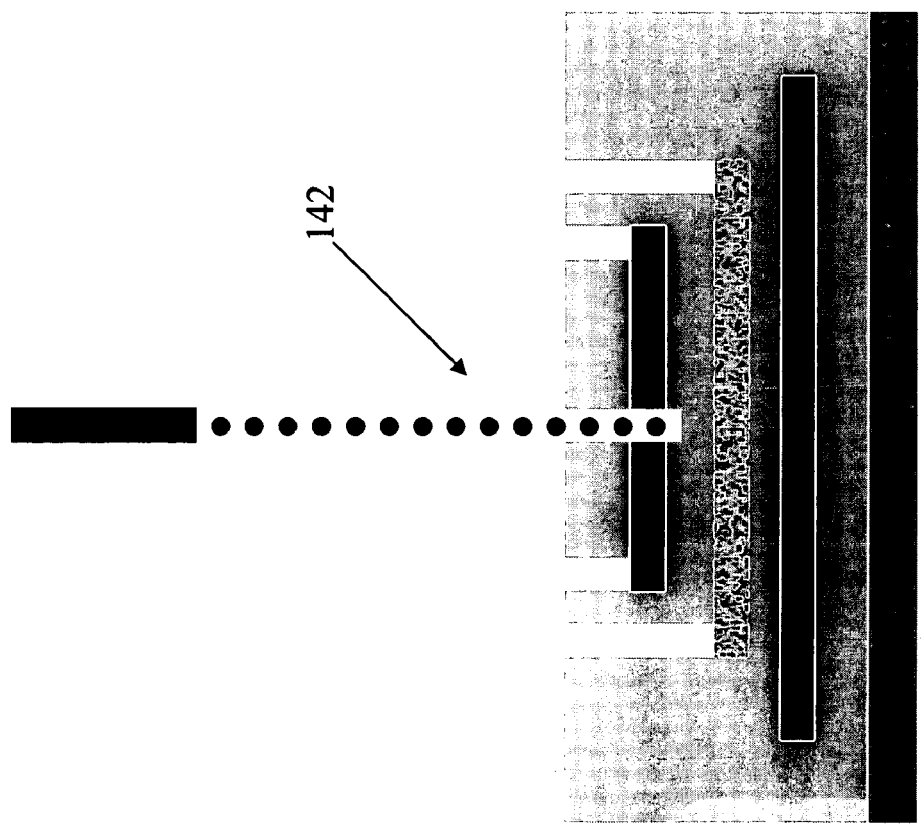
FIG. 8 is an alternate embodiment for performing the last step using ion milling.

As shown in FIG. 8, the deposition of photoresist layer 136 and etching of the micro feature 70 may be replaced with an ion milling (or focused ion beam) step 142 to form micro feature 70. Ion milling may be preferable because higher aspect ratios and deeper trenches can be manufactured. Packaging of the micro sensor is also less likely to cause contamination inside the deep micro feature if it is performed prior to the forming of the micro feature. Forming the micro feature after packaging can not be performed using chemical etching because the chemical used to etch would damage the package. Ion milling could be done after packaging. Micro features with different aspect ratios and depth can be manufactured on the same die when using ion milling, (this is much more difficult with etching). Moreover, there is an economic incentive to manufacture the sensor using ion milling. When etching the micro feature, all die on the same wafer have the same depth. Standard microelectronics processing can be used to manufacture the micro sensor except for the last fabrication step and small quantities of micro sensors with a particular depth can be manufactured using ion milling.

Figure 9:
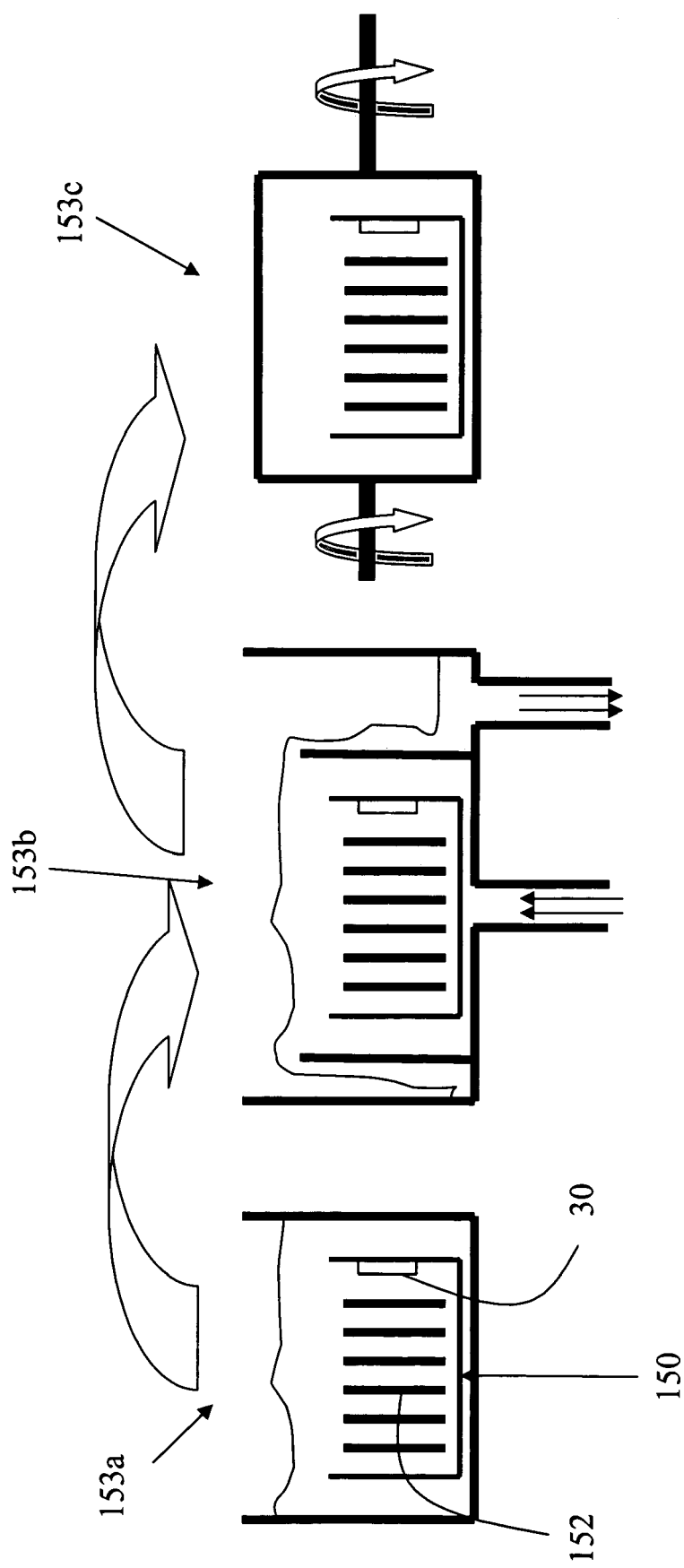
FIG. 9 is a diagram of a clean/rinse/dry process using the micro sensor.
Figure 10:
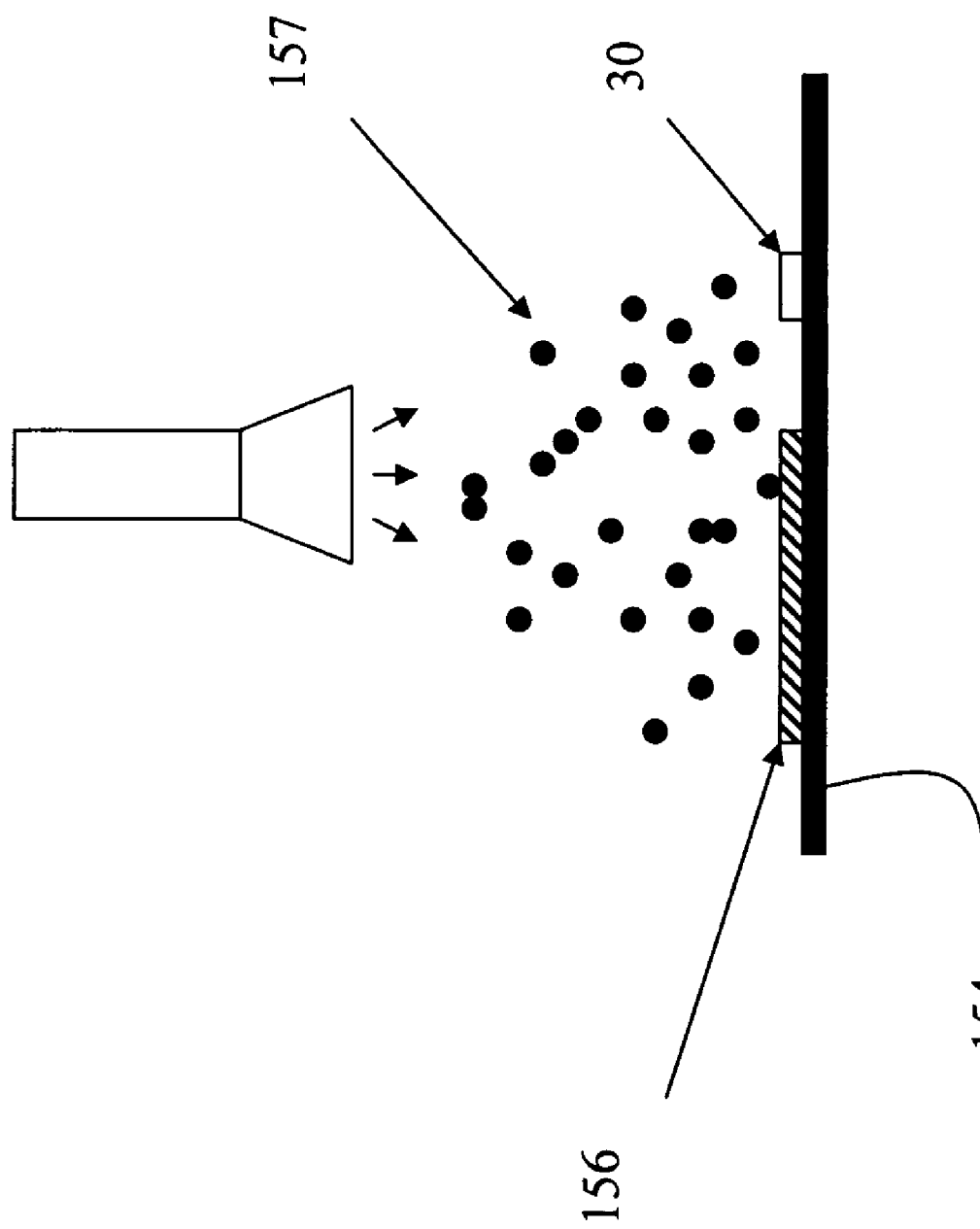
FIG. 10 is a diagram of an alternate clean/rinse/dry process using the micro sensor.
Figure 11:
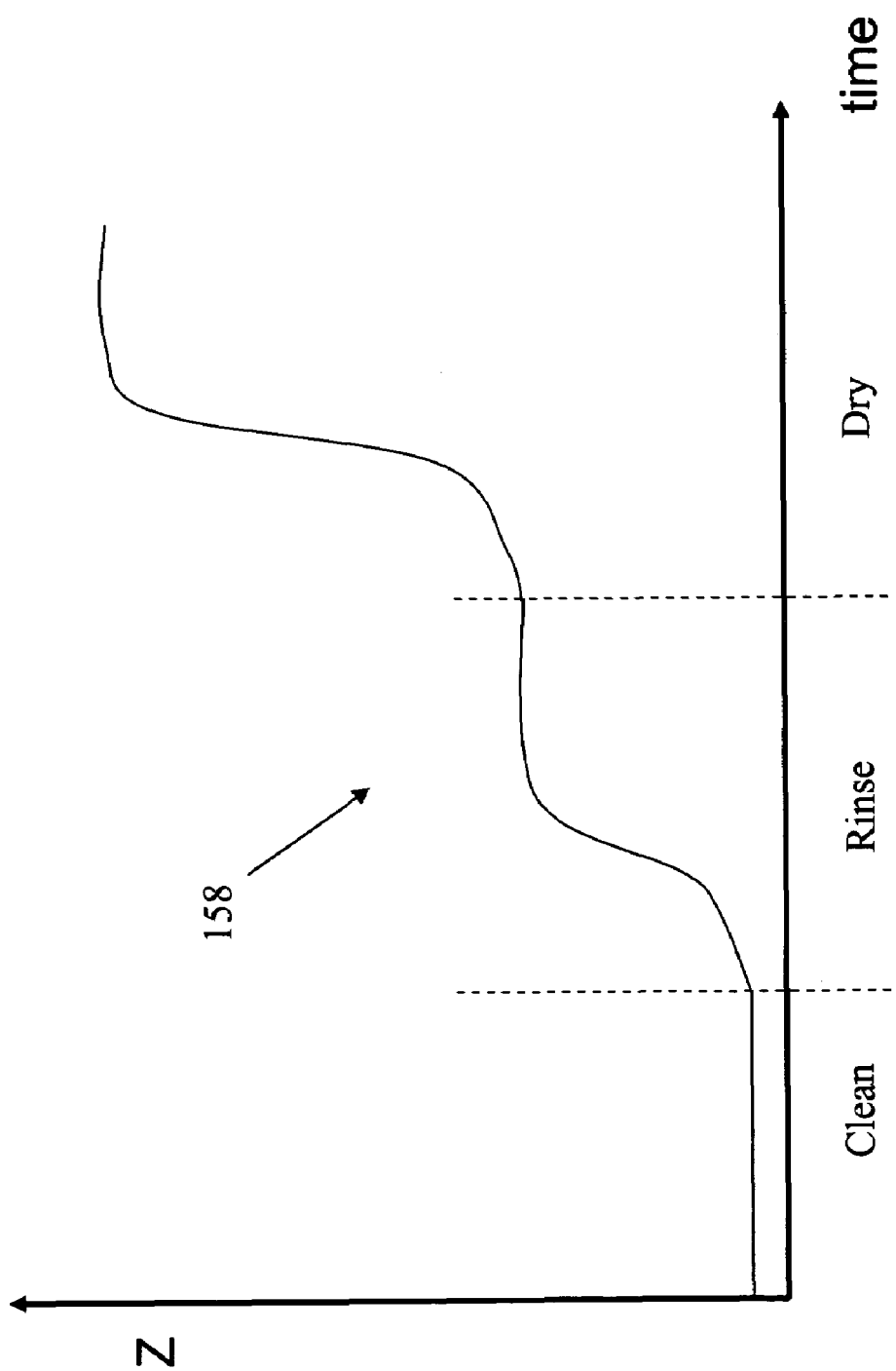
FIG. 11 is a plot of impedance vs. time for a representative clean/rinse/dry cycle.

The use of the micro sensor 30 to monitor the clean/rinse/dry process is illustrated in FIGS. 9-11. Typically, micro sensor 30 would be placed in a cleaning solution of a known ion concentration to calibrate the sensor. Once calibrated the micro sensor may be inserted in a cassette 150 with a number of other product wafers 152 and processed through a sequence of clean/rinse/dry baths 153a-153c as shown in FIG. 9 or mounted on a chuck 154 with a single wafer 156 and subjected to a sequence of clean/rinse/dry sprays 157 as shown in FIG. 10.

As shown in FIG. 11, as the micro sensor passes through the clean/rinse/dry cycle the measured impedance 158 changes fairly dramatically from a very low impedance during cleaning, to a moderate impedance during rinse and finally to a much higher impedance when the drying process is completed. By first calibrating the sensor to the allowable surface concentration, the rinse and dry process duration can be optimized. Also, by first calibrating the process and then monitoring the impedance during an actual production run, the wafers can be transferred from one process to the next to ensure adequate clean/rinse/dry without wasting time or chemicals. Alternatively, the sharp increases in impedance levels and subsequent leveling can be used to trigger a transfer to the next processing stage. If process calibration is both accurate and stable enough, e.g. the times to transfer, then it is possible that the micro sensor may not be needed during the actual production runs, but is merely used to periodically confirm that the process performance is still within specifications.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A micro sensor, comprising:
   a first dielectric layer;
   a conductive layer on said first dielectric layer;
   a second dielectric layer on said conductive layer; and
   a void micro feature that extends through said second dielectric layer and said conductive layer thereby defining first and second electrodes in said conductive layer on opposite sides of the micro feature,
   an impedance analyzer that applies ac measurement signal between the electrodes to measure the impedance of the micro feature as the ratio between an ac measurement signal voltage and current, said micro sensor having first and second parasitic capacitances between the first and second electrodes and a surrounding environment;
   a conductive guard layer in at least one of the first and second dielectric layers, said void micro feature extending through said guard layer to define first and second guards on opposite sides of the micro feature; and
   first and second buffers each having a first input connected to opposite sides of the impedance analyzer and a second input connected to a buffer output, said buffers having unity gain bandwidth larger than the ac measurement signal frequency to supply current to the first and second guards so that their voltages closely track the the ac measurement signals applies to the first and second electrodes, respectively, to separately shield each said first and second electrode from the surrounding environment and thereby reduce the loss of measurement signal through each of the first and second parasitic capacitances.

2. The micro sensor of claim 1, further comprising a porous dielectric material in said void micro feature.

3. The micro sensor of claim 1, wherein the porous dielectric material is a different material than said first and second dielectric layers.

4. The micro sensor of claim 1, wherein the micro feature has an aspect ratio of at least 3-to-1.

5. The micro sensor of claim 1, further comprising a dielectric covering layer that covers the second dielectric layer and the micro feature.

6. The micro sensor of claim 5, wherein the dielectric covering layer is a different dielectric material than said first and second dielectric layers.

7. The micro sensor of claim 1, wherein the first dielectric layer comprises a dielectric layer on a non-dielectric substrate.

8. The micro sensor of claim 7, wherein the first and second parasitic capacitances are between the electrodes and the substrate, the conductive guard layer comprising a first conductive layer in the first dielectric layer that defines said first and second guards between said first and second electrodes and said substrate.

9. The micro sensor of claim 8, wherein a top surface of the sensor defines a fluid-solid interface with third and fourth parasitic capacitances between the electrodes and said interface, the conductive guard layer comprising a second conductive layer in the second dielectric layer that defines third and fourth guards between said first and second electrodes and said interface, said first and second buffers supplying current to said third and fourth guards, respectively so that their voltage closely track the ac measurement signals applied to the first and second electrodes, respectively.

10. The micro sensor of claim 9, wherein the conductive guard layer further comprises a first and a second conductive perimeter around the electrodes that electrically connects said first and third electrodes and said second and fourth electrodes, respectively.

11. The micro sensor of claim 10, wherein the conductive guard layer surrounds the electrodes except at the edges of the micro feature and at the electrode contacts.

12. The micro sensor of claim 1, wherein a top surface of the micro sensor defines a fluid-solid interface, the conductive guard layer comprising a first conductive layer in the second dielectric layer that defines said first and second guards between said first and second electrodes and said interface.

13. The micro sensor of claim 1, wherein the micro feature is substantially perpendicular to the stack of dielectric and conductive layers.

14. A micro sensor, comprising:

a dielectric;

a micro feature in or on the dielectric;

first and second electrodes in or on the dielectric layer on opposite sides of the micro feature;

an impedance analyzer that applies an ac measurement signal between the electrodes to measure the impedance of the micro feature as the ratio between an ac measurement signal voltage and current;

first and second conductive guards in the dielectric on opposite sides of the micro feature; and first and second buffers each having a first input connected to the impedance analyzer and a second input connected to a buffer output, said buffers having unity gain bandwidth larger than the ac measurement signal frequency to supply current to the first and second conductive guards, respectively, so that their voltages closely track the ac measurement signal voltages applied to the first and second electrodes, respectively.

15. The micro sensor of claim 14, wherein said micro feature comprises a porous dielectric material.

16. The micro sensor of claim 14, wherein said micro feature is a void micro feature in said dielectric.

17. The micro sensor of claim 14, wherein the conductive guards surrounds the respective electrodes except at the edges of the micro feature and at the electrode contacts.

18. The micro sensor of claim 14, wherein the dielectric is supported on a substrate, said conductive guards lying in the dielectric between the electrodes and the substrate.

19. The micro sensor of claim 14, wherein a top surface of the dielectric defines a fluid-solid interface, said conductive guards lying in the dielectric between the electrodes and the interface.

* * * * *